United States Patent [19]

Samejima et al.

[11] Patent Number: 5,320,683

[45] Date of Patent: * Jun. 14, 1994

[54] AZEOTROPIC OR AZEOTROPIC-LIKE COMPOSITION OF HYDROCHLOROFLUOROPROPANE

[75] Inventors: Shunichi Samejima, Tokyo; Kenroh Kitamura, Fujisawa; Naohiro Watanabe, Chiba; Teruo Asano, Yokohama; Toru Kamimura, Ichihara; Shinsuke Morikawa, Yokohama, all of Japan

[73] Assignee: Asahi Glass Company Ltd., Tokyo, Japan

[*] Notice: The portion of the term of this patent subsequent to May 26, 2009 has been disclaimed.

[21] Appl. No.: 941,269

[22] Filed: Sep. 4, 1992

Related U.S. Application Data

[62] Division of Ser. No. 543,850, Jul. 27, 1990, abandoned.

[30] Foreign Application Priority Data

| | | | |
|---|---|---|---|
| Feb. 6, 1989 | [JP] | Japan | 1-25641 |
| Feb. 6, 1989 | [JP] | Japan | 1-25652 |
| Feb. 6, 1989 | [JP] | Japan | 1-25682 |
| Feb. 6, 1989 | [JP] | Japan | 1-25683 |
| Apr. 18, 1989 | [JP] | Japan | 1-96464 |

[51] Int. Cl.$^5$ .......................... B08B 3/00; C23G 5/028; H05C 3/26

[52] U.S. Cl. ............................................. 134/40; 8/142; 134/12; 134/31; 134/38; 252/172; 252/194; 252/DIG. 9

[58] Field of Search .................. 134/12, 31, 38, 39, 134/40, 42; 252/67, 68, 162, 170, 171, 172, 194, 305, 364, DIG. 9; 8/142

[56] References Cited

U.S. PATENT DOCUMENTS

| | | | |
|---|---|---|---|
| 2,462,402 | 2/1949 | Joyce | 260/653 |
| 2,582,242 | 1/1952 | Eberl | 252/364 |
| 2,653,393 | 7/1954 | Eberl | 252/364 |
| 3,080,430 | 3/1963 | Cohen | 260/653 |
| 3,476,819 | 11/1969 | Trischler | 260/653 |
| 3,804,769 | 4/1974 | Lomas | 252/171 |
| 4,465,609 | 8/1984 | Dens et al. | 252/67 |
| 4,647,391 | 3/1987 | Bertocchio et al. | 252/69 |
| 4,873,021 | 10/1989 | Gorski et al. | 252/364 |
| 4,947,881 | 8/1990 | Magio et al. | 134/40 |
| 4,961,869 | 10/1990 | Eggers et al. | 252/170 |
| 4,970,013 | 11/1990 | Merchant | 252/69 |
| 4,985,168 | 1/1991 | Ohmure et al. | 252/67 |
| 4,988,455 | 1/1991 | Magio et al. | 252/171 |
| 4,995,908 | 2/1991 | Buchwald | 252/171 |
| 5,116,426 | 5/1992 | Asano et al. | 134/40 |

FOREIGN PATENT DOCUMENTS

| | | |
|---|---|---|
| 1086450 | 9/1980 | Canada . |
| 0347924 | 12/1989 | European Pat. Off. . |
| 0381216 | 8/1990 | European Pat. Off. . |
| 2575174 | 6/1986 | France ............... 252/67 |
| 89/12674 | 12/1989 | PCT Int'l Appl. ....... 252/172 |
| 1562026 | 3/1980 | United Kingdom . |
| 91/05035 | 4/1991 | World Int. Prop. O. . |
| 91/05082 | 4/1991 | World Int. Prop. O. . |
| 91/05083 | 4/1991 | World Int. Prop. O. . |

OTHER PUBLICATIONS

Paleta et al. *Collection Czechoslov. Commin.* vol. 36 pp. 1867–1874 1971 (no month available).

Asahi Glass Company, News Article published Feb. 6, 1989.

Russian Publication, Application No. 4 831 103/04 (097 742), filed Aug. 10, 1990.

Patent Abstracts of Japan, vol. 13, No. 255 (C-606)(3603), Jun. 13, 1989, & JP, A, 160694 (Daikin Ind Ltd) Mar. 7, 1989.

Patent Abstracts of Japan, vol. 13, No. 124 (C-570)(3472), Mar. 27, 1989 & JP, A, 63295699 (Daikin Ind Ltd), Dec. 2, 1988.

Coffman et al., *Journal of American Chemical Society* Mar. 1949 pp. 979–980.

*Primary Examiner*—Linda Skaling
*Attorney, Agent, or Firm*—Oblon, Spivak, McClelland, Maier & Neustadt

[57] ABSTRACT

A hydrochlorofluoropropane azeotropic or azeotropic-like composition comprising at least two members selected from the group consisting of hydrochlorofluoropropanes of the formula I:

$$CH_aCl_bF_cCF_2CH_xCl_yF_z \qquad (I)$$

wherein $a+b+c=3$, $x+y+z=3$, $a+x \geq 1$, $b+y \geq 1$, and $0 \leq a,b,c,x,y,z \leq 3$.

8 Claims, No Drawings

AZEOTROPIC OR AZEOTROPIC-LIKE COMPOSITION OF HYDROCHLOROFLUOROPROPANE

This is a division of application Ser. No. 07/543,850 filed on Jul. 27, 1990, now abandoned.

TECHNICAL FIELD

The present invention relates to a novel hydrochlorofluoropropane azeotropic or azeotropic-like composition which can be used as a chlorofluorocarbon alternative and which has excellent properties as a solvent and so on.

BACKGROUND ART

Chlorofluorocarbon compounds (hereinafter referred simply as CFCs) have little toxicity and are, in many cases, non-flammable and chemically stable. Various CFCs having different boiling points are available. By virtue of such properties, 1,1,2-trichloro-1,2,2-trifluoroethane (R113) is used as a solvent or a blowing agent; trichloromonofluoromethane (R11) is used as a blowing agent or a propellant; and dichlorodifluoromethane (R12) is used as a propellant or a refrigerant.

Chemically stable R11, R12 and R113 have long lifetime in the troposphere and reach the stratosphere, where they will be dissociated by solar radiation to release chlorine radicals, which initiate a chain reaction with ozone and deplete the ozone layer. Accordingly, the regulations for limiting the use of such conventional CFCs have been implemented. Therefore, a research has been actively conducted to develop a CFC alternative which scarcely depletes the ozone layer.

DISCLOSURE OF THE INVENTION

It is an object of the present invention to provide a mixture comprising novel hydrochlorofluoropropanes having 3 carbon atoms, which has various excellent properties equal to conventional CFCs and which is useful as a CFC alternative.

The present invention provides a hydrochlorofluoropropane azeotropic or azeotropic-like composition comprising at least two members selected from the group consisting of hydrochlorofluoropropanes of the formula I:

$$CH_aCl_bF_cCF_2CH_xCl_yF_z \qquad (I)$$

wherein $a+b+c=3$, $x+y+z=3$, $a+x \geq 1$, $b+y'1$, and $0 \leq a,b,c,x,y,z \leq 3$.

The composition of the present invention is non-flammable and may take a form of an azeotropic composition or an azeotropic-like composition. Particularly when used as a solvent, it provides properties equal or superior to conventional 1,1,2-trichlorotrifluoroethane (R113). Therefore, it is very useful as an alternative for R113. Further, no substantial change was observed in the composition when boiling or evaporating. Therefore, it may be used in the same manner as a conventional single CFC, whereby it has a merit in that no substantial change in the conventional technique is required.

BEST MODE FOR CARRYING OUT THE INVENTION

The hydrochlorofluoropropanes of the formula I in the present invention contain a hydrogen atom and a fluorine atom as essential elements and may further contain a chlorine atom. Specifically, they include the following compounds:

$CClF_2CF_2CHCl_2$ (R224ca)

$CCl_2FCF_2CHClF$ (R224cb)

$CF_3CF_2CHCl_2$ (R225ca)

$CClF_2CF_2CHClF$ (R225cb)

$CClF_2CF_2CH_2Cl$ (R234cc)

$CHF_2CF_2CHClF$ (R235ca)

$CH_3CF_2CCl_2F$ (R243cc)

$CHF_2CF_2CH_2Cl$ (R244ca)

$CH_2ClCF_2CH_2Cl$ (R252ca)

$CHCl_2CF_2CH_3$ (R252cb)

$CH_3CF_2CH_2Cl$ (R262ca)

$CHF_2CF_2CCl_2F$ (R225cc)

$CHClFCF_2CHClF$ (R234ca)

$CHF_2CF_2CHCl_2$ (R234cb)

$CH_2FCF_2CCl_2F$ (R234cd)

$CF_3CF_2CH_2Cl$ (R235cb)

$CClF_2CF_2CH_2F$ (R235cc)

$CH_2ClCF_2CHClF$ (R243ca)

$CH_2FCF_2CHCl_2$ (R243cb)

$CH_2FCF_2CHClF$ (R244cb)

$CClF_2CF_2CH_3$ (R244cc)

$CH_2FCF_2CH_2Cl$ (R253ca)

$CH_3CF_2CHClF$ (R253cb)

$CF_3CF_2CHClF$ (R226ca)

$CClF_2CF_2CHF_2$ (R226cb)

$CCl_3CF_2CHCl_2$ (R222c)

$CCl_2FCF_2CHCl_2$ (R223ca)

$CCl_3CF_2CHClF$ (R223cb)

$CCl_3CF_2CHF_2$ (R224cc)

$CHCl_2CF_2CHCl_2$ (R232ca)

$CCl_3CF_2CH_2Cl$ (R232cb)

$CCl_2FCF_2CH_2Cl$ (R233cb)

$CHCl_2CF_2CHClF$ (R233ca)

$CCl_3CF_2CH_2F$ (R233cc)

$CCl_3CF_2CH_3$ (R242cb)

$CHCl_2CF_2CH_2Cl$ (R242ca)

Among them, preferred are R225ca, R225cb, R244ca, R244cb, R235ca and R243cc.

The composition comprising R225ca, R225cb and R244ca of the present invention usually comprises from 12 to 92% by weight of R225ca, from 3 to 77% by weight of R225cb and from 3 to 69% by weight of R244ca, preferably from 51 to 64% by weight of R225ca, from 4 to 16% by weight of R225cb and from 26 to 39% by weight of R244ca. More preferably, it is an azeotropic composition comprising about 58% by weight of R225ca, about 10% by weight of R225cb and about 32% by weight of R244ca.

The composition comprising R225ca and R225cb of the present invention has excellent azeotropic-like characteristics over the entire range of the blend ratio of R225ca and R225cb. Therefore, there is no particular restriction as to the proportions of R225ca and R225cb in the composition of the present invention. However, the composition preferably comprises from 0.01 to 99.99% by weight of R225ca and from 0.01 to 99.99% by weight of R225cb.

The composition comprising R225cb and R244ca of the present invention usually comprises from 27 to 67% by weight of R225cb and from 33 to 73% by weight of R244ca, preferably from 37 to 57% by weight of R225cb and from 43 to 63% by weight of R244ca. More preferably, it is an azeotropic composition comprising about 47% by weight of R225cb and about 53% by weight of R244ca.

The composition comprising R225ca and R244ca of the present invention usually comprises from 52 to 92% by weight of R225ca and from 8 to 48% by weight of R244ca, preferably from 62 to 82% by weight of R225ca and from 18 to 38% by weight of R244ca. More preferably, it is an azeotropic composition comprising about 72% by weight of R225ca and about 28% by weight of R244ca.

When R225ca and R243cc are used, the composition of the present invention usually comprises from 56 to 95% by weight of R225ca and from 4 to 44% by weight of R243cc, preferably from 66 to 86% by weight of R225ca and from 14 to 34% by weight of R243cc. More preferably, it is an azeotropic composition comprising about 76% by weight of R225ca and about 24% by weight of R243cc.

When R225cb and R244cb are employed, the composition usually comprises from 47 to 87% by weight of R225cb and from 13 to 53% by weight of R244cb, preferably from 57 to 77% by weight of R225cb and from 23 to 43% by weight of R244cb. More preferably, it is an azeotropic composition comprising about 67% by weight of R225cb and about 33% by weight of R244cb.

When R225cb and R243cc are used, the composition usually comprises from 43 to 83% by weight of R225cb and from 17 to 57% by weight of R243cc, preferably from 53 to 73% by weight of R225cb and from 27 to 47% by weight of R243cc. More preferably, it is an azeotropic composition comprising about 63% by weight of R225cb and about 37% by weight of R243cc.

When R244ca and R243cc are used, the composition usually comprises from 48 to 88% by weight of R244ca and from 12 to 52% by weight of R243cc, preferably from 58 to 78% by weight of R244ca and from 22 to 42% by weight of R243cc. More preferably, it is an azeotropic composition comprising about 68% by weight of R244ca and about 32% by weight of R243cc.

When R244ca and R244cb are used, the composition usually comprises from 5 to 95% by weight of R244ca and from 5 to 95% by weight of R244cb, preferably from 10 to 90% by weight of R244ca and from 10 to 90% by weight of R244cb.

When R244cb and R243cc are used, the composition usually comprises from 32 to 72% by weight of R244cb and from 28 to 68% by weight of R243cc, preferably from 42 to 62% by weight of R244cb and from 38 to 58% by weight of R243cc. More preferably, it is an azeotropic composition comprising about 52% by weight of R244cb and about 48% by weight of R243cc.

When R235ca and R243cc are used, the composition usually comprises from 70 to 99% by weight of R235ca and from 1 to 30% by weight of R243cc, preferably from 80 to 95% by weight of R235ca and from 5 to 20% by weight of R243cc. More preferably, it is an azeotropic composition comprising about 90% by weight of R235ca and about 10% by weight of R243cc.

To the composition of the present invention, other components may further be incorporated depending upon its application. For example, when the composition is used as a solvent, it may suitably contain a hydrocarbon such as pentane, isopentane, hexane, isohexane, neohexane, heptane, isoheptane, 2,3-dimethylbutane or cyclopentane; a nitroalkane such as nitromethane, nitroethane or nitropropane; a triazole such as 1,2,3-benzotriazole; an amine such as diethylamine, triethylamine, isopropylamine, butylamine or isobutylamine; an amylene such as $\alpha$-, $\beta$- or $\gamma$-amylene or $\alpha$- or $\beta$-isoamylene; an alcohol such as methanol, ethanol, n-propylalcohol, i-propylalcohol, n-butylalcohol, i-butylalcohol, s-butylalcohol or t-butylalcohol; a phosphite such as triphenyl phosphite or tributyl phosphite; an ether such as methyl cellosolve, tetrahydrofuran or 1,4-dioxane; an epoxide such as 1,2-butylene oxide or epichlorohydrin; a ketone such as acetone, methyl ethyl ketone or methyl butyl ketone; an ester such as ethyl acetate, propyl acetate or butyl acetate; a furan such as N-methylpyrrole; a chlorinated or brominated hydrocarbon such as dichloromethane, trichloroethane, trichloroethylene, tetrachloroethylene, trans-1,2-dichloroethylene, cis 1,2-dichloroethylene, 1-chloropropane, 2-chloro-2-methylpropane or 2-bromopropane; or a CFC hydrochlorofluorocarbon or hydrofluorocarbon other than those of the present invention, such as 1,1,2-trichlorotrifluoroethane, 1,1,2-trichloro-2,2-difluoroethane, tetrachloro-1,2-difluoroethane, 1,1-dichloro-2,2,2-trifluoroethane, 1,2-dichloro-1,1-difluoroethane, 1,2-dichloro-1-fluoroethane, 1,1-dichloro-1-fluoroethane, 1,1-dichloro-2,3,3,3-tetrafluoropropene-1, trans-3-chloro-1,1,1,2,4,4,5,5,5-nonfluoropentene-2, cis-3-chloro 1,1,1,2,4,4,5,5,5-nonafluoropentene-2 or 1,1,1,2,2,5,5,6,6,6-decafluorohexane.

The content of such additional components in the composition of the present invention is not particularly limited, but for the purpose of improving or controlling the solibility or obtaining a suitable boiling point or non-flammability, the content is usually from 0 to 50% by weight, preferably from 1 to 40% by weight. Preferably such incorporation will bring about an azeotropic or azeotropic-like composition. Further, to give the mixture a high level of stabilizing effect, it is effective to incorporate a stabilizer. The content of such additional components is usually from 1 ppm to 10% by weight, preferably from 10 ppm to 5% by weight. Further, the composition of the present invention may further contain various cleaning assistants, surfactants, emulsifying agents, water, etc.

The hydrochlorofluoropropane azeotropic or azeotropic-like composition of the present invention is useful for various purposes, for example, as a blowing agent and so on, like conventional CFCs. It is particularly useful as a solvent, since it provides a solvency equivalent or superior to conventional R113. Specific applications as the solvent include a removing agent for flux, grease, oil, wax or ink, a coating solvent, an extracting agent, a cleaning or water-removing agent for various articles made of glass, ceramics, plastic, rubber or metal, particularly for semiconductor devices, electronic components, electronic circuit boards, electrical devices, precision machine parts or optical lenses. Further, it is useful as a resist developer, a resist-removing agent or a buff polishing and cleaning agent. As a cleaning method, manual wiping, dipping, spraying, shaking, ultrasonic cleaning or vapor cleaning may be employed.

Now, the present invention will be described in further detail with reference to Examples. However, it should be understood that the present invention is by no means restricted by such specific Examples.

EXAMPLES 1

1,000 g of a solvent composition having the following composition was charged to a distillation flask, and using a packed distillation column which contained approximately 20 theoretical plates, distillation was conducted under atmospheric pressure.

| Composition | % by weight |
| --- | --- |
| R225ca (boiling point: 51.1° C.) | 60 |
| R225cb (boiling point: 56.1° C.) | 10 |
| R244ca (boiling point: 54° C.) | 30 |

As a result, 440 g of a distillation fraction was obtained. The fraction was analyzed by gas chromatography and was found to have the following composition.

| Composition | % by weight |
| --- | --- |
| R225ca | 58 |
| R225cb | 10 |
| R244ca | 32 |

EXAMPLE 2

Using the composition of the present invention (R225ca/R225cb/R244ca=58 wt. %/10 wt. %/32 wt. %), a test for cleaning machine oil was conducted.

A SUS 304 test piece (25 mm×30 mm×2 mm in thickness) was immersed in machine oil (CQ-30, manufactured by Nippon Sekiyu K.K.) and then immersed for 5 minutes in the above composition of the present invention. As a result, it was confirmed that the machine oil can be removed satisfactorily as in the case of R113.

EXAMPLE 3

Flammability of the composition of Example 2 (R225ca/R225cb/R244ca=58 wt. %/10 wt. %/32 wt. %) was measured with Tag closed cup flash point tester (JIS K2265), and the composition had no flash point and was confirmed to be non-flammable.

EXAMPLE 4

1,000 g of a solvent composition having the following composition was charged to a distillation flask, and using a packed distillation column which contained approximately 20 theoretical plates, distillation was conducted under atmospheric pressure.

| Composition | % by weight |
| --- | --- |
| R225ca (boiling point: 51.1° C.) | 50 |
| R225cb (boiling point: 56.1° C.) | 50 |

As a result, 320 g of a fraction at 54° C. was obtained. The fraction was analyzed by gas chromatography and was found to have the following composition.

| Composition | % by weight |
| --- | --- |
| R225ca | 48 |
| R225cb | 52 |

EXAMPLE 5

1,000 g of a solvent composition having the following composition was charged to a distillation flask, and using a packed distillation column which contained approximately 20 theoretical plates, distillation was conducted under atmospheric pressure.

| Composition | % by weight |
| --- | --- |
| R225ca (boiling point: 51.1° C.) | 80 |
| R225cb (boiling point: 56.1° C.) | 20 |

As a result, 300 g of a fraction at 53° C. was obtained. The fraction was analyzed by gas chromatography and was found to have the following composition.

| Composition | % by weight |
| --- | --- |
| R225ca | 79 |
| R225cb | 21 |

EXAMPLE 6

1,000 g of a solvent composition having the following composition was charged to a distillation flask, and using a packed distillation column which contained approximately 20 theoretical plates, distillation was conducted under atmospheric pressure.

| Composition | % by weight |
| --- | --- |
| R225ca (boiling point: 51.1° C.) | 20 |
| R225cb (boiling point: 56.1° C.) | 80 |

As a result, 290 g of a fraction at 55° C. was obtained. The fraction was analyzed by gas chromatography and was found to have the following composition.

| Composition | % by weight |
| --- | --- |
| R225ca | 19 |
| R225cb | 81 |

EXAMPLE 7

Using the composition of the present invention (R225ca/R225cb=50 wt. %/50 wt. %), a test for cleaning machine oil was conducted.

A SUS-304 test piece (25 mm x 30 mm x 2 mm in thickness) was immersed in machine oil (CQ-30, manufactured by Nippon Sekiyu K.K.) and then immersed for 5 minutes in the above composition of the present invention. As a result, it was confirmed that the machine oil can be removed satisfactorily as in the case of R113.

EXAMPLE 8

Flammability of the composition of the present invention (R225ca/R225cb=50 wt. %/50 wt. %) was measured with Tag closed cup flash point tester (JIS K2265), and the composition had no flash point and was confirmed to be non-flammable.

EXAMPLE 9

1,000 g of a solvent composition having the following composition was charged to a distillation flask, and using a packed distillation column which contained approximately 20 theoretical plates, distillation was conducted under atmospheric pressure.

| Composition | % by weight |
| --- | --- |
| R225cb (boiling point: 56.1° C.) | 50 |
| R244ca (boiling point: 54° C.) | 50 |

As a result, 400 g of a fraction at 53° C. was obtained. The fraction was analyzed by gas chromatography and was found to have the following composition.

| Composition | % by weight |
| --- | --- |
| R225cb | 47 |
| R244ca | 53 |

EXAMPLE 10

Using the composition of the present invention (R225cb/R244ca=47 wt. %/53 wt. %), a test for cleaning machine oil was conducted.

A SUS-304 test piece (25 mm×30 mm×2 mm in thickness) was immersed in machine oil (CQ-30, manufactured by Nippon Sekiyu K.K.) and then immersed for 5 minutes in the above composition of the present invention. As a result, it was confirmed that the machine oil can be removed satisfactorily as in the case of R113.

EXAMPLE 11

Flammability of the composition of Example 10 (R225cb/R244ca=47 wt. %/53 wt. %) was measured with Tag closed cup flash point tester (JIS K2265), and the composition had no flash point and was confirmed to be non-flammable.

EXAMPLE 12

1,000 g of a solvent composition having the following composition was charged to a distillation flask, and using a packed distillation column which contained approximately 20 theoretical plates, distillation was conducted under atmospheric pressure.

| Composition | % by weight |
| --- | --- |
| R225ca (boiling point: 51.1° C.) | 70 |
| R244ca (boiling point: 54° C.) | 30 |

As a result, 390 g of a fraction at 51° C. was obtained. The fraction was analyzed by gas chromatography and was found to have the following composition.

| Composition | % by weight |
| --- | --- |
| R225ca | 72 |
| R244ca | 28 |

EXAMPLE 13

Using the composition of the present invention (R225ca/R244ca=72 wt. %/28 wt. %), a test for cleaning machine oil was conducted.

A SUS-304 test piece (25 mm×30 mm×2 mm in thickness) was immersed in machine oil (CQ-30, manufactured by Nippon Sekiyu K.K.) and then immersed for 5 minutes in the above composition of the present invention. As a result, it was confirmed that the machine oil can be removed satisfactorily as in the case of R113.

EXAMPLE 14

Flammability of the composition of Example 13 (R225ca/R244ca=72 wt. %/28 wt. %) was measured with Tag closed cup flash point tester (JIS K2265), and the composition had no flash point and was confirmed to be non-flammable.

EXAMPLE 15

1,000 g of a solvent composition having the following composition was charged to a distillation flask, and using a packed distillation column which contained approximately 20 theoretical plates, distillation was conducted under atmospheric pressure.

| Composition | % by weight |
| --- | --- |
| R225ca (boiling point: 51.1° C.) | 80 |
| R243cc (boiling point: 60.2° C.) | 20 |

As a result, 400 g of a fraction at 51° C. was obtained. The fraction was analyzed by gas chromatography and was found to have the following composition.

| Composition | % by weight |
| --- | --- |
| R225ca | 76 |
| R243cc | 24 |

EXAMPLE 16

Using the composition of Example 15 (R225ca/R243cc=76 wt. %/24 wt. %), a test for cleaning machine oil was conducted.

A SUS 304 test piece (25 mm×30 mm×2 mm in thickness) was immersed in machine oil (CQ-30, manufactured by Nippon Sekiyu K.K.) and then immersed for 5 minutes in the above composition of the present invention. As a result, it was confirmed that the machine oil can be removed satisfactorily as in the case of R113.

EXAMPLE 17

Flammability of the composition of Example 15 (R225ca/R243cc=76 wt. %/24 wt. %) was measured with Tag closed cup flash point tester (JIS K2265), and the composition had no flash point and was confirmed to be non-flammable.

EXAMPLE 18

1,000 g of a solvent composition having the following composition was charged to a distillation flask, and using a packed distillation column which contained approximately 20 theoretical plates, distillation was conducted under atmospheric pressure.

| Composition | % by weight |
| --- | --- |
| R225cb (boiling point: 56.1° C.) | 70 |
| R244cb (boiling point: 58° C.) | 30 |

As a result, 450 g of a fraction at 56° C. was obtained. The fraction was analyzed by gas chromatography and was found to have the following composition.

| Composition | % by weight |
| --- | --- |
| R225cb | 67 |
| R244cb | 33 |

EXAMPLE 19

Using the composition of Example 18 (R225cb/R244cb=67 wt. %/33 wt. %), a test for cleaning machine oil was conducted.

A SUS-304 test piece (25 mm×30 mm×2 mm in thickness) was immersed in machine oil (CQ-30, manufactured by Nippon Sekiyu K.K.) and then immersed for 5 minutes in the above composition of the present invention. As a result, it was confirmed that the machine oil can be removed satisfactorily as in the case of R113.

EXAMPLE 20

1,000 g of a solvent composition having the following composition was charged to a distillation flask, and using a packed distillation column which contained approximately 20 theoretical plates, distillation was conducted under atmospheric pressure.

| Composition | % by weight |
| --- | --- |
| R225cb (boiling point: 56.1° C.) | 60 |
| R243cc (boiling point: 60.2° C.) | 40 |

As a result, 390 g of a fraction at 54° C. was obtained. The fraction was analyzed by gas chromatography and was found to have the following composition.

| Composition | % by weight |
| --- | --- |
| R225cb | 63 |
| R243cc | 37 |

EXAMPLE 21

Using the composition of Example 20 (R225cb/R244cc =63 wt. %/37 wt. %), a test for cleaning machine oil was conducted.

A SUS-304 test piece (25 mm×30 mm×2 mm in thickness) was immersed in machine oil (CQ-30, manufactured by Nippon Sekiyu K.K.) and then immersed for 5 minutes in the above composition of the present invention. As a result, it was confirmed that the machine oil can be removed satisfactorily as in the case of R113.

EXAMPLE 22

1,000 g of a solvent composition having the following composition was charged to a distillation flask, and using a packed distillation column which contained approximately 20 theoretical plates, distillation was conducted under atmospheric pressure.

| Composition | % by weight |
| --- | --- |
| R244ca (boiling point: 54° C.) | 70 |
| R243cc (boiling point: 60.2° C.) | 30 |

As a result, 430 g of a fraction at 53° C. was obtained. The fraction was analyzed by gas chromatography and was found to have the following composition.

| Composition | % by weight |
| --- | --- |
| R244ca | 68 |
| R243cc | 32 |

EXAMPLE 23

Using the composition of Example 22 (R244ca/R243cc=68 wt. %/32 wt. %), a test for cleaning machine oil was conducted.

A SUS-304 test piece (25 mm×30 mm×2 mm in thickness) was immersed in machine oil (CQ-30, manufactured by Nippon Sekiyu K.K.) and then immersed for 5 minutes in the above composition of the present invention. As a result, it was confirmed that the machine oil can be removed satisfactorily as in the case of R113.

EXAMPLE 24

1,000 g of a solvent composition having the following composition was charged to a distillation flask, and using a packed distillation column which contained approximately 20 theoretical plates, distillation was conducted under atmospheric pressure.

| Composition | % by weight |
| --- | --- |
| R244ca (boiling point: 54° C.) | 70 |
| R244cb (boiling point: 58° C.) | 30 |

As a result, 360 g of a fraction was obtained. The fraction was analyzed by gas chromatography and was found to have the following composition.

| Composition | % by weight |
| --- | --- |
| R244ca | 69.5 |
| R244cb | 30.5 |

EXAMPLE 25

Using the composition of R244ca/R244cb=70 wt. %/30 wt. %, a test for cleaning machine oil was conducted.

A SUS-304 test piece (25 mm×30 mm×2 mm in thickness) was immersed in machine oil (CQ-30, manufactured by Nippon Sekiyu K.K.) and then immersed for 5 minutes in the above composition of the present invention. As a result, it was confirmed that the machine oil can be removed satisfactorily as in the case of R113.

EXAMPLE 26

1,000 g of a solvent composition having the following composition was charged to a distillation flask, and using a packed distillation column which contained approximately 20 theoretical plates, distillation was conducted under atmospheric pressure.

| Composition | % by weight |
|---|---|
| R244cb (boiling point: 58° C.) | 50 |
| R243cc (boiling point: 60.2° C.) | 50 |

As a result, 480 g of a fraction at 56° C. was obtained. The fraction was analyzed by gas chromatography and was found to have the following composition.

| Composition | % by weight |
|---|---|
| R244cb | 52 |
| R243cc | 48 |

EXAMPLE 27

Using the composition of Example 26 (R244cb/R243cc =52 wt. %/48 wt. %), a test for cleaning machine oil was conducted.

A SUS-304 test piece (25 mm×30 mm×2 mm in thickness) was immersed in machine oil (CQ-30, manufactured by Nippon Sekiyu K.K.) and then immersed for 5 minutes in the above composition of the present invention. As a result, it was confirmed that the machine oil can be removed satisfactorily as in the case of R113.

EXAMPLE 28

1,000 g of a solvent composition having the following composition was charged to a distillation flask, and using a packed distillation column which contained approximately 20 theoretical plates, distillation was conducted under atmospheric pressure.

| Composition | % by weight |
|---|---|
| R235ca (boiling point: 43.9° C.) | 85 |
| R243cc (boiling point: 60.2° C.) | 15 |

As a result, 430 g of a fraction at 45° C. was obtained. The fraction was analyzed by gas chromatography and was found to have the following composition.

| Composition | % by weight |
|---|---|
| R235ca | 90 |
| R243cc | 10 |

EXAMPLE 29

Using the composition of Example 28 (R235ca/R243cc=90 wt. %/10 wt. %), a test for cleaning machine oil was conducted.

A SUS-304 test piece (25 mm×30 mm×2 mm in thickness) was immersed in machine oil (CQ-30, manufactured by Nippon Sekiyu K.K.) and then immersed for 5 minutes in the above composition of the present invention. As a result, it was confirmed that the machine oil can be removed satisfactorily as in the case of R113.

INDUSTRIAL APPLICABILITY

The hydrochlorofluoropropane composition of the present invention has properties as excellent as the conventional CFCs and has an azeotropic composition of an excellent azeotropic-like properties. Therefore, it shows no substantial change during boiling or evaporating. It can be used in the same manner as a conventional single CFC and thus has a merit that no substantial change of the conventional technique is required for its use.

We claim:

1. A method of removing material from a substrate, comprising applying to said material a composition which consists essentially of 12–92% by weight 3,3-dichloro-1,1,1,2,2-pentafluoropropane (R225ca), 3–77% by weight 1,3-dichloro-1,1,2,2,3-pentafluoropropane (R225cb) and 3–69% by weight 3-chloro-1,1,2,2-tetrafluoropropane (R244ca).

2. The method of claim 1, wherein said composition consists essentially of 51–64% by weight R225ca, 4–16% by weight R225cb and 26–29% by weight R244ca.

3. A method of removing material from a substrate, comprising applying to said material a composition which consists essentially of 27–67% by weight 1,3-dichloro-1,1,2,2,3-pentafluoropropane (R225cb) and 33–73% by weight 3-chloro-1,1,2,2-tetrafluoropropane (R244ca).

4. The method of claim 3, wherein said composition consists essentially of 37–57% by weight R225cb and 43–63% by weight R244ca.

5. A method of removing materials from a substrate comprising applying to said material a composition which consists essentially of 52–92% by weight 3,3-dichloro-1,1,1,2,2-pentafluoropropane (R225Ca) and 8–48% by weight 3-chloro-1,1,2,2-tetrafluoropropane (R244ca).

6. The method of claim 5, wherein said composition consists essentially of 62–82% by weight R225ca and 18–38% by weight R244ca.

7. A method of removing material from a substrate, comprising applying to said material a composition consisting essentially of 3,3-dichloro-1,1,1,2,2-pentafluoropropane (R225ca) and 1,3-dichloro-1,1,2,2,3-pentafluoropropane (R225cb).

8. The method of claim 7, wherein both said R225cb and R225ca are present in amounts of 0.01–99.99% by weight.

* * * * *